(12) United States Patent
Russo (10) Patent No.: US 10,918,848 B1
(45) Date of Patent: Feb. 16, 2021

(54) HIGH FLOW ENTERNAL CONNECTOR SYSTEM

(71) Applicant: Ronald D. Russo, Naples, FL (US)

(72) Inventor: Ronald D. Russo, Naples, FL (US)

( * ) Notice: Subject to any disclaimer, the term of this patent is extended or adjusted under 35 U.S.C. 154(b) by 0 days.

(21) Appl. No.: 15/731,481

(22) Filed: Jun. 16, 2017

(51) Int. Cl.
    *A61M 39/10* (2006.01)
    *A61J 15/00* (2006.01)

(52) U.S. Cl.
    CPC .......... *A61M 39/10* (2013.01); *A61J 15/0003* (2013.01); *A61J 15/0015* (2013.01); *A61J 15/0076* (2015.05); *A61M 2039/1038* (2013.01)

(58) Field of Classification Search
    CPC ................ A61J 15/0076; A61J 15/0015; A61J 15/0003; A61M 39/1027; A61M 39/1038; A61M 39/105; A61M 2039/1038; A61M 39/10; A61M 2039/1094; A61M 2039/1083; A61M 2039/1088
    See application file for complete search history.

(56) References Cited

U.S. PATENT DOCUMENTS

| | | | | |
|---|---|---|---|---|
| 4,668,217 | A * | 5/1987 | Isono | A61M 39/10 604/29 |
| 6,418,997 | B1 * | 7/2002 | Tamai | B65H 37/007 118/257 |
| 9,656,022 | B1 | 5/2017 | Russo | |
| 2009/0306598 | A1 * | 12/2009 | Arcaro | A61M 39/0613 604/167.03 |
| 2014/0066840 | A1 * | 3/2014 | Mantell | A61M 13/003 604/26 |
| 2015/0119863 | A1 * | 4/2015 | Christensen | A61M 39/10 604/539 |
| 2015/0238747 | A1 * | 8/2015 | Russo | A61M 39/1011 604/533 |
| 2017/0014616 | A1 | 1/2017 | Davis et al. | |
| 2017/0065810 | A1 | 3/2017 | Hess et al. | |
| 2017/0203086 | A1 * | 7/2017 | Davis | A61J 15/0076 |

OTHER PUBLICATIONS

ISO-80369-3 ANSI Standards Attached Jul. 1, 2016 pp. 10-15.
"Tubing misconnections—a persistent and potentially deadly occurrence," The Joint Comission Sentinel Event Alert, Apr. 3, 2006, Issue 36.
Guenter et al., "Enteral Feeding Misconnections: A Consotium Position Statment," The Joint Cornission Journal on Quality and Patient Safety, May 2008, vol. 34 No. 5.
"Avoiding Catheter and Tubing Mis-Connections," Patient Safety Solutions,May 2007, vol. 1, Solution 7.

* cited by examiner

*Primary Examiner* — Lauren P Farrar
*Assistant Examiner* — Hamza A Darb
(74) *Attorney, Agent, or Firm* — Bryan L. Loeffler, Esq.; Loeffler IP Group, P.A.

(57) ABSTRACT

A two-part enteral connector system having first and second parts. The first part has a housing with an internal fluid flow passageway and the housing further includes external thread elements and a tip projection portion. The second part also has a housing with an internal fluid flow passageway and mating internal thread elements and resilient internal sealing surface area such that the first part is threadably engageable with the second part in an ISO 80369-3 thread compatible connection to form a liquid tight sealable engagement between the two parts such that the joined fluid flow passageways provide a high flow fluid flow passageway in excess of the 2.95 mm flow path of the existing ISO 80369-3 enteral small-bore connector flow path.

23 Claims, 12 Drawing Sheets

FIG. 1

PRIOR ART

HIGH FLOW ENTERNAL CONNECTOR SYSTEM

Applicant claims the benefit of U.S. Provisional Patent Application No. 62/493,163 filed Jun. 23, 2016 entitled "High Flow Enteral Connector System" and U.S. Provisional Patent Application No. 62/495,081 filed Aug. 31, 2016 entitled "Accurate Dosage Enteral Syringe."

BACKGROUND OF THE INVENTION

Enteral feeding tubes are used to deliver enteral nutrition to medical patients who cannot eat or swallow normal food. These tubes can be naso-enteric tubes or gastrostomy tubes placed in the gastro-intestinal tract. Enteral nutrition either can be commercially prepared liquid such as Ensure® enteral formula or can be home-prepared food that is diluted and blenderized. Commercial liquid formula can be administered using pump gravity feed or bolus syringe feeding, while home-blenderized food is typically delivered using a large bore enteral syringe. The flow path of the large bore enteral syringe is typically in the 4 mm internal diameter tip range to accommodate the more viscous blenderized home patient enteral diet.

In order to avoid misconnections between intravenous (I.V.) catheters and enteral feeding tubes, the International Organization for Standardization (ISO) has recently promulgated and issued ISO Standard 80369-3 for small-bore connectors for access ports on enteral feeding sets and patient interfaces.

The ISO 80369-3 Standard for small-bore enteral connectors is being implemented by many medical device manufacturers both in the United States and internationally. The Standard comprises two components neither of which forms a mating engagement with I.V. luer components or catheters.

While it is a positive that these new ISO 80369-3 compliant components do not mate with I.V. luers, these components have encountered difficulties and problems in actual patient and clinical use. Notably, both components are now threaded screw-type connections with a reduced internal flow path of only 2.95 mm which although sufficient for pump pressure feeding, presents flow constriction problems and passageway clogging with gravity and bolus syringe feedings and especially with the more viscous blenderized food.

The present high flow enteral connector system invention maintains compatibility with the ISO 80369-3 screw thread design standard while providing a high flow internal flow passageway design to overcome the clogging and restricting flow path problems inherent in the new ISO 80369-3 Standard.

Toward this end, the present invention has been conceived. Other objects, features, and advantages of the invention shall become apparent as the description thereof proceeds when considered in connection with the accompanying drawings.

SUMMARY OF THE INVENTION

A high flow enteral feeding connector is disclosed which is compatible with the ISO 80369-3 screw thread connection design. The system is comprised of two parts of preferably plastic injection molded single patient use components typically molded from rigid ABS, polycarbonate, resilient polyethylene or Santoprene® resilient elastomer. Both parts are generally circular in configuration.

The first part is molded from rigid plastic having a circular housing with an internal fluid flow passageway with an external portion having a threadable engagement element. A circular generally tapered tip projection portion is positioned below the threaded portion.

The second component part also has a circular housing with an internal fluid flow passageway and the second part also has a mating internal screw thread configuration that forms a threadable engagement with the first part.

Most importantly, the second part has a resilient internal circular sealing surface area positioned below the internal threaded configuration. Once the first part is fully threadably engaged with the second part, the first part rigid circular tapered tip projection portion engages and forms a fluid tight compressive contact sealing engagement with the resilient internal circular sealing surface on the first part. The unique reconfigured design of both the first part and second part permits compatibility with the ISO 80369-3 thread engagement connection while still maintaining incompatibility with I.V. luer connectors.

Most importantly, the unique design of both components significantly increases the internal fluid flow passageways from the maximum fluid flow internal diameter of only 2.95 mm on the ISO 80369-3 components up to a maximum of 5.75 mm in internal diameter as part of the uniqueness of the present invention. That increase even exceeds the 4 mm internal flow path of most enteral bolus syringes making the present invention design capable of use with all pump and gravity sets along with bolus syringes and especially for use with viscous blenderized food that the existing ISO 80369-3 connector cannot accommodate. This substantial increase in flow volume also prevents clogging and gives longevity of use and reduced component replacement cost, and the present system is totally compatible with all ISO 80369-3 systems.

The present invention design is also easier to clean and maintain than the ISO 80369-3 male connector thus reducing the potential for bacterial contamination from the existing ISO 80369-3 constricted internal configuration and inaccessible circular moat and deep crevice areas.

These and other advantages will become apparent from a review of the accompanying drawings and the detailed description of the invention.

DESCRIPTION OF THE DRAWINGS

In the drawings which illustrate the best mode presently contemplated for carrying out the present invention.

DETAILED DESCRIPTION OF THE INVENTION

Figure 1:
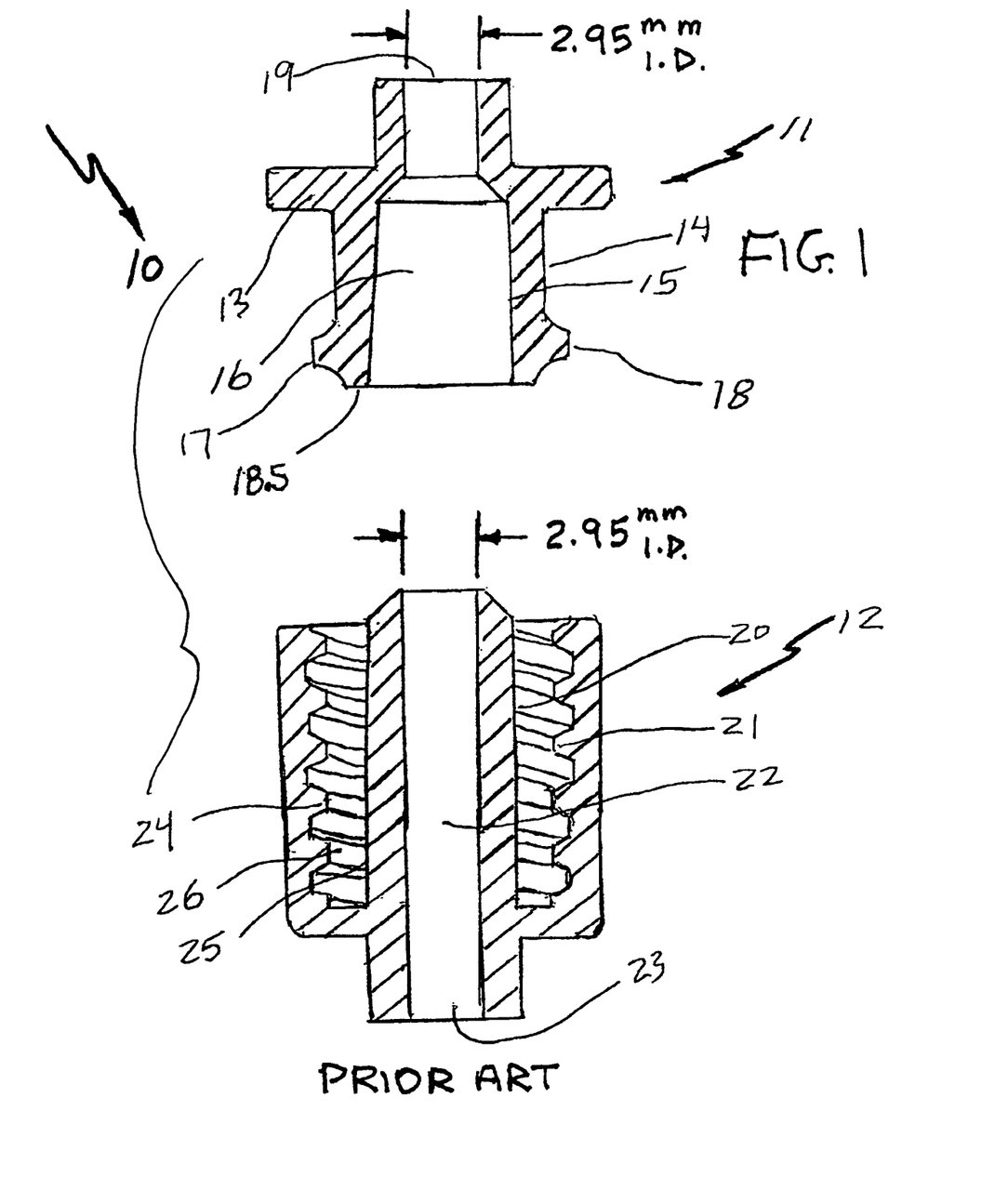
FIG. 1 is a cross-sectional view of both the male and female connector components of the prior art ISO 80369-3 enteral connector standard.

It is important to first understand the design, configuration, and performance of the prior art ISO 80369-3 Standard enteral connector 10 as shown in FIG. 1 hereafter referred to as ISO connector. The ISO connector 10 comprises a female small-bore connector 11 and a male small-bore connector 12. Both connectors 11 and 12 are typically injection molded from Scaled D rigid durometer medical grade plastic such as ABS or polycarbonate.

The female ISO connector 11 has an outer body 13 having a circular housing 14 whose dimensional length is fixed by the ISO Standard at 7 mm in length regardless of whether the female ISO connector 11 is used in a pump or gravity feed delivery set or a syringe connector.

Figure 2:
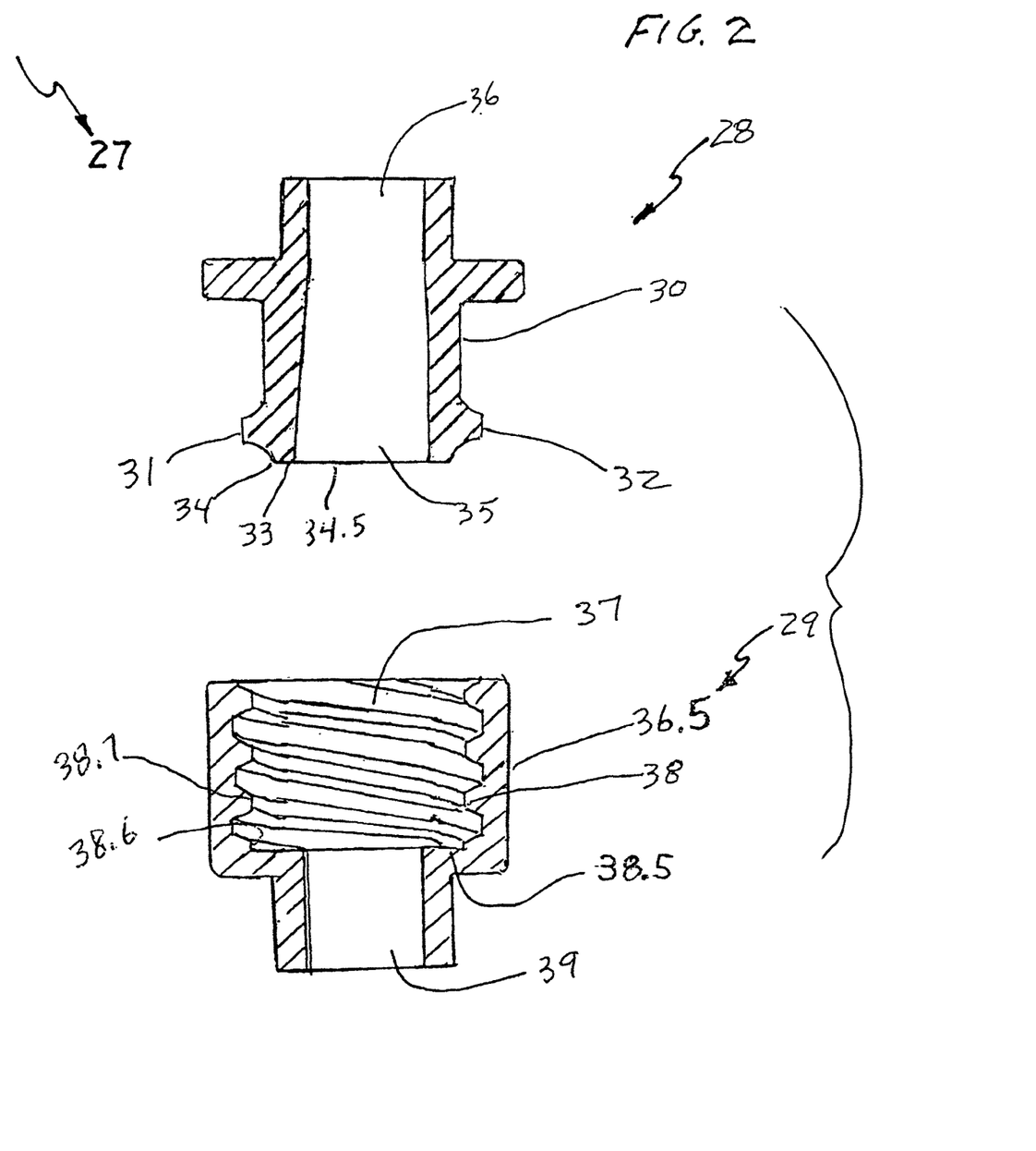
FIG. 2 is a comparative cross-sectional view of both the first part and second part of the high flow enteral connector system of the present invention.

The 7 mm standardized length of the female ISO connector 11 is very important as this component can be utilized and is fully compatible with the present invention depicted in FIG. 2. The female ISO connector 11 has an interior socket portion 15 with a length of 7.14 mm. The circular housing 14 has an internal fluid flow passageway 16 along with external thread engagement elements 17 and 18 that are partial thread elements. The housing 14 further has a circular tapered tip projection 18.5 positioned below the external thread engagement elements 17 and 18.

The fluid flow passageway 16 extends to fluid flow inlet passageway 19, which is dimensionally fixed by the ISO Standard to be only 2.95 mm in internal diameter. The 2.95 mm inlet fluid flow passageway 19 is the limiting flow passageway within the entire ISO connector 10.

The socket portion 15 on female ISO connector 11 forms a rigid socket to rigid cone connection 20 on male connector 12 once the thread external elements 17 and 18 on female connector 11 are threadably engaged with the mating internal thread engagement elements 21 on the male connector 12 to form a rigid socket to rigid cone taper lock sealing engagement.

Likewise, the male connector 12 has an internal fluid flow passageway 22 of 2.95 mm, which is the same as the limiting passageway 19 on the female connector 11.

The length of the depth of the internal thread elements 21 on the male ISO connector 12 can vary in length by more than 10 mm and must exceed the circular housing 14 length of 7 mm to give extended dimensional clearance to permit a liquid tight engagement fit between the socket 15 and cone 20 caused by the mating threaded engagement between the external socket threaded elements 17 and 18 and the internal threaded elements 21.

Once the female ISO connector 11 and male connector 12 are threadably joined and mated, the limiting 2.95 mm flow passageway inlet 19 is maintained throughout the male connector passageway 22 to the outlet passageway 23. This limiting 2.95 mm flow passageway permits a sufficient flow through the female ISO connector 11 when the connector is part of a single use pump formula delivery set. However, a 2.95 mm flow passageway is not dimensionally sufficient to deliver more viscous formula by gravity set feed and is totally inadequate to provide such sufficient flow for blenderized food. Further, the male ISO connector 12 usually remains as part of the patient's feeding tube apparatus such that the 2.95 mm flow passageway 22 is easily clogged especially if the male connector 12 is not routinely irrigated or syringe flushed.

Another drawback of the patient side male ISO connector 12 is that the internal thread inner diameter 24 is standardized to 8.65 mm in diameter while the outside diameter 25 of the cone is 5.65 mm in diameter. This construction leaves a circumferential gap or deep crevice or moat 26 of only 1.5 mm in width and usually 10 mm in depth length which allows for spilled formula to collect in the crevice or moat area 26 that is virtually impossible to clean or flush during repeated use for up to 30 days, creating a breeding ground for contamination. Reinfusing this accumulated contaminated material is a leading cause of bacterial intestinal infections that can have serious consequences especially for immunocompromised patients.

ISO connector cleaning brushes are now being marketed to try to clean the ISO connector deep crevice moat 26. However, the cleaning brushes may serve to make the infectious aspects of the ISO connector worse by spraying accumulated material around patient areas.

By comparison, FIG. 2 depicts the present two part enteral connector system 27 having first part 28 and second part 29. The first part 28 has an outer circular housing 30 dimensionally configured in conformance as an ISO 80369-3 female small-bore connector as shown in FIG. 1. The housing 30 length is the same ISO 80369-3 7 mm length and the external thread engagement elements 31 and 32 are the same ISO 80369-3 elements 17 and 18 from FIG. 1.

The external thread elements 31 and 32 on the housing 30 are shown as partial molded in external lug threads in FIG. 2 that are easier and less expensive to mold than a full spiral external thread element that requires an unscrewing mechanism to mold. However, a full spiral molded in external thread element is often preferable especially on a syringe because a full spiral thread provides maximum thread engagement force being applied to circular tip projection portion 33. The first part 28 must be molded from rigid plastic such as ABS or polycarbonate to maintain thread integrity and the stiffness of the circular tip projection portion 33 positioned below the external thread engagement elements 31 and 32 on the housing 30.

Further, the circular tip projection portion 33 now preferably has a circular radius corner 34 to project a rigid concentrated sealing point. The circular tip projection portion 33 is positioned at the outlet end 34.5 of the inner flow passageway 35. The inner flow passageway 35 has been increased to 5.7 mm. Most importantly, the fluid flow inlet passageway 36 is now increased to 5.3 mm compared to the ISO connector-limiting inlet 19 from FIG. 1 of only 2.95 mm.

As such, the connector system 27 depicted in FIG. 2 now has a first part connector 28 having an internal fluid flow passageway 36 which exceeds the limiting 2.95 mm inner diameter of the ISO 80369-3 Standard depicted and shown in FIG. 1.

The second part 29 of system 27 also has circular housing 36.5 injection molded from a resilient low density polyethylene or Santoprene® elastomer whose resiliency is preferably between 80 to 90 Shore A durometer. Durometers below 80 are too soft and durometers above 90 are too rigid to provide a leakproof seal with the first part 28.

The second part 29 has a large internal non-obstructed fluid flow passageway 37 of at least 8.5 mm in diameter with mating internal thread engagement elements 38 whose depth length does not exceed 6.82 mm.

It is very important that the internal thread engagement elements 38 on the second part 29 be fully molded in internal spiral threads as shown to prevent any partial thread disengagement or thread jumping from the first part 28 especially if the first part 28 uses partial molded in external lug threads 31 and 32 as depicted in FIG. 2.

The outlet passageway 39 can now also be increased to 5.3 mm to match the inlet passageway 36 on the first part 28. As such, the connector system 27 depicted in FIG. 2 now also has a second part connector 29 having an internal fluid flow passageway 39 which exceeds the limiting 2.95 mm inner diameter of the ISO 80369-3 Standard depicted and shown in FIG. 1. In summary, connector system 27 can now have a high flow system wherein both the first part 28 fluid flow passageway 36 and the second part 29 fluid flow passageway 39 exceeds the limiting 2.95 mm inner diameter of the ISO 80369-3 depicted and shown in FIG. 1. The housing 36.5 now includes resilient internal circular sealing surface area 38.5 positioned below the internal thread engagement element 38. Resiliency results from the fact that housing 36.5 is molded from resilient Shore A 80 to 90 low-density polyethylene or Santoprene® elastomer.

Once the tapered tip projection 33 on the first part 28 is fully threadably engaged with the second part 29, the tip projection 33 forms a fluid tight compressive contact sealing engagement with the resilient internal circular sealing surface area 38.5 within the second part 29 housing 36 which is positioned at the bottom end 38.6 of the thread depth length 38.7 within the circular housing 36.5.

The fluid tight compressive contact sealing engagement between the first part 28 and second part 29 is achieved because the standardized length of the external thread engagement element portion 31 and 32 of 7 mm on the first part 28 exceeds the shorter undersized 6.82 mm depth length of the internal thread element portion 38 of the second part 29 to form a solid compressive interference dimensional fit between the rigid tip protection 33 on the first part 28 and the resilient internal circular sealing surface 38.5 on the first part 28 when both parts 28 and 29 are fully threadably engaged. This fluid tight compressive contact sealing engagement is more clearly shown in FIG. 5.

Importantly, to insure this compressive dimensional interference fit, the molding of the second part 29 internal thread portion 38 depth of 6.82 mm must be closely maintained such that the depth of the element 38 within the second part circular housing 36.5 does not exceed the depth of 6.82 mm.

Figures 3, 4:
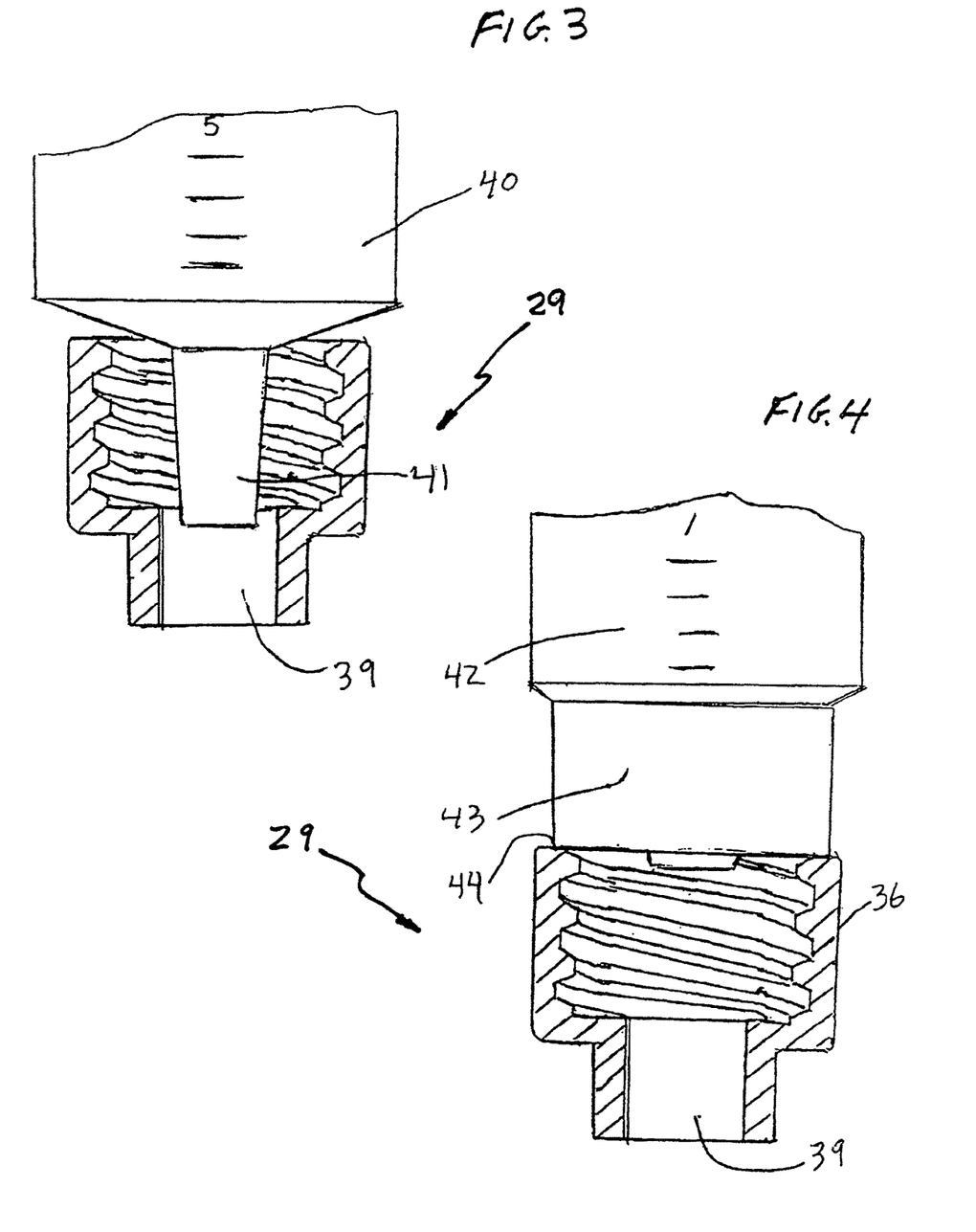
FIG. 3 is a partial cross-sectional view of a luer tip I.V. syringe incapable of forming an engagement interlocking fit with the second part of the high flow enteral connector system of the present invention.
FIG. 4 is a partial cross-sectional view of a luer lock tip I.V. syringe incapable of forming an engagement interlocking fit with the second part of the high flow enteral connector system of the present invention.

Further, FIGS. 3 and 4 are partial cross-sectional views of luer tip and luer lock syringes incapable of forming an engagement interlocking fit with the second part 29. FIG. 3 depicts a luer slip tip syringe 40 having an ISO luer dimensioned tip 41 of 4 mm incapable of forming an interlocking fit with the second part 29 outlet 39 having an oversized internal outlet 39 internal diameter of 5.3 mm. Likewise, from FIG. 4 luer lock tip syringe 42 having an ISO luer dimensioned tip 43 forms only a butt stop fit 44 with outer housing 36.5. Luer tips 41 and 43 are dimensionally defined by the ISO ANSI 1986 luer standard.

As such, the second part 29 of the system 27 prevents any misconnection with I.V. luer tip syringes. This maintains the misconnection capabilities of the present invention system 27 to prevent any possible interlocking fit usage of second part 29 that usually remains with the patient feeding tube along with any I.V. luer devices.

Figure 5:
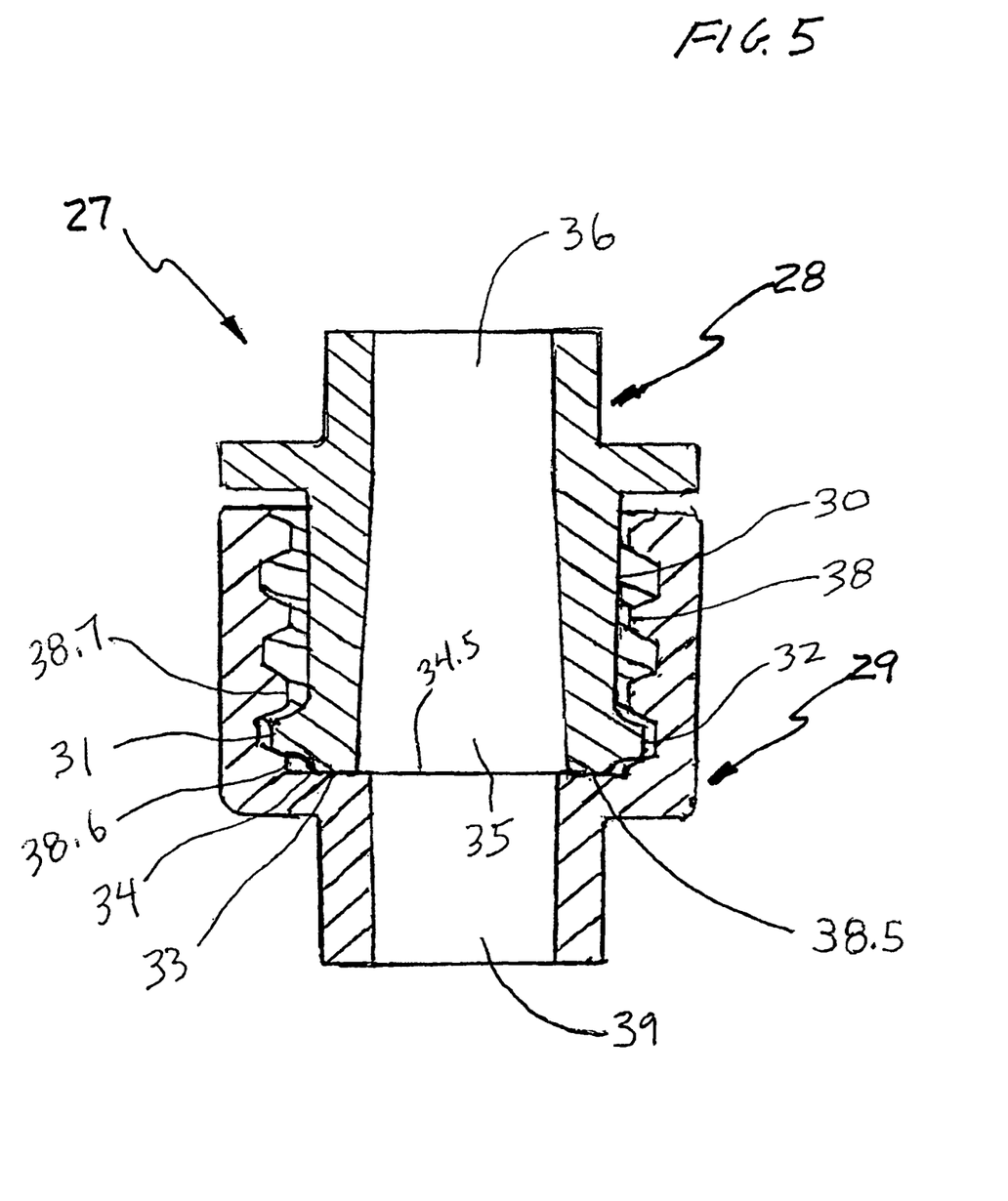
FIG. 5 is a cross-sectional view of the fluid flow tight sealing engagement threadably formed between the first part and the second part of the high flow enteral connector system of the present invention.

FIG. 5 is an enlarged cross-sectional view of the first part 28 threadably matingly engaged with second part 29. As can be seen from FIG. 5, once the first part 28 is fully threadably engaged with the second part 29, inlet passageway 36, inner passageway 35, and outlet passageway 39, all are aligned to provide a high flow enteral connector system 27 having a continuous internal flow path of up to 5.75 mm in diameter.

Liquid nutrition, even viscous blenderized nutrition often used by at-home patients, is permitted to flow between the fluid flow passageways 36 and 35 on the first part on through the fluid flow passageway 39 on the second part without leakage when both parts are fully threadably engaged. As such, all internal flow passages 36, 35, and 39 far exceed the limiting 2.95 mm flow path of the prior art ISO connector shown and described from FIG. 1.

Figures 6, 6A:
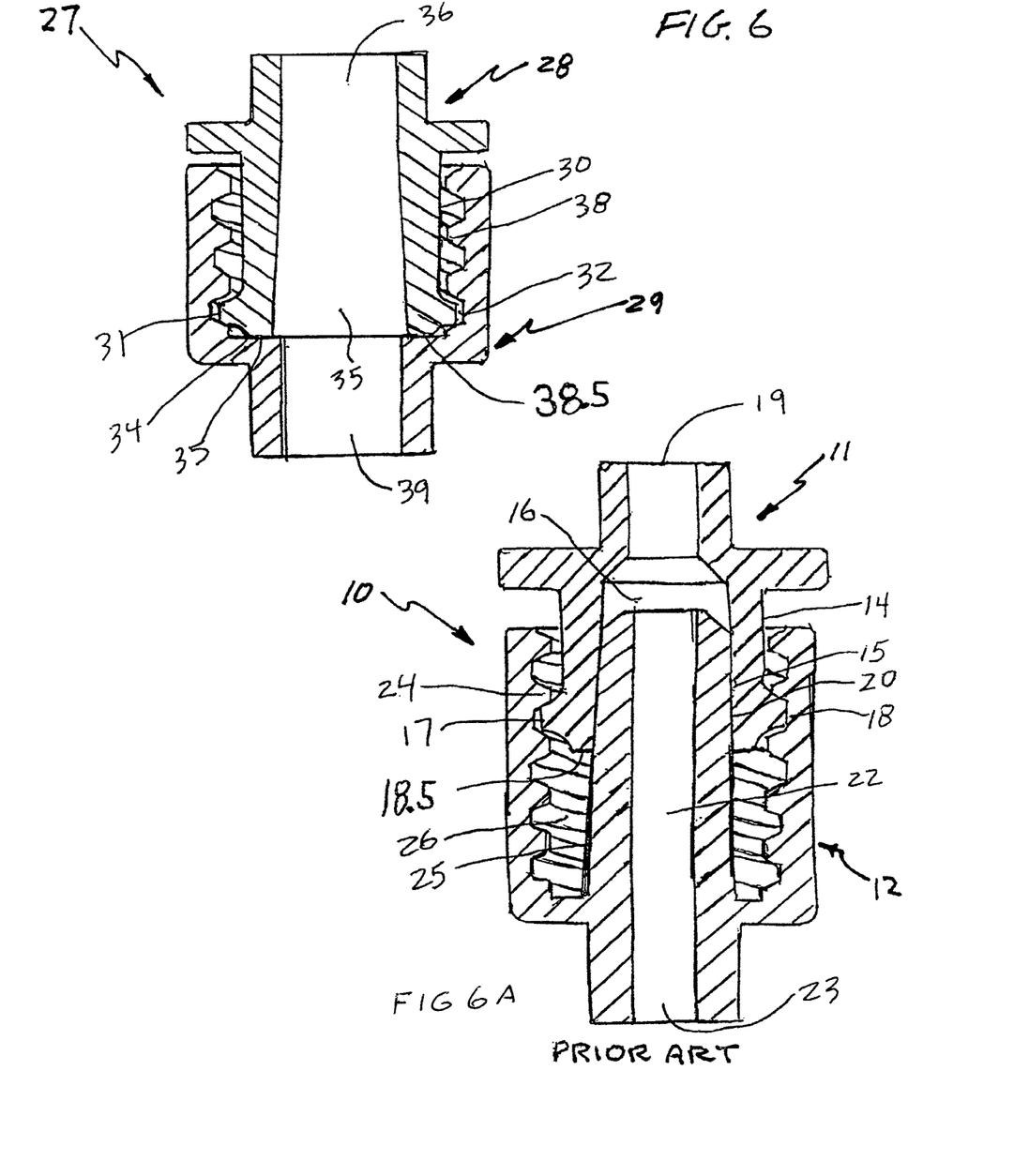
FIGS. 6 and 6A are comparative cross-sectional views illustrating the engagement mechanisms and flow path differences between the high flow enteral connector system of the present invention and the ISO 80369-3 enteral connector system.

FIGS. 6 and 6A are comparative cross-sectional views clearly depicting the engagement mechanisms and flow path differences between the high flow enteral connector system 27 of the present invention compared to the prior art ISO connector system 10 from FIG. 1. All the respective descriptive items are clearly identified in FIG. 6 between the present high flow enteral connector system 27 when compared to the constricted flow path system of the prior art ISO connector 10. Note that the continuous flow path 36, 35, and 39 is up to 5.75 mm in the present invention 27 whereas the flow path is only 2.95 mm in the prior art system 10 shown in FIG. 6A.

The mathematic formula for determining the flow volume through a connector is $V=D^4$ where V=flow volume and D equals the inner diameter multiplied to the fourth power. Using this formula, the present invention flow volume is equal to 5.75 mm diameter to the fourth power or 1093 whereas the prior art connector is only 75.7 using this same formula. This means that the present invention flow volume is over 14 times greater than the prior art connector while still using the same dimensional screw thread engagement.

Figure 7:
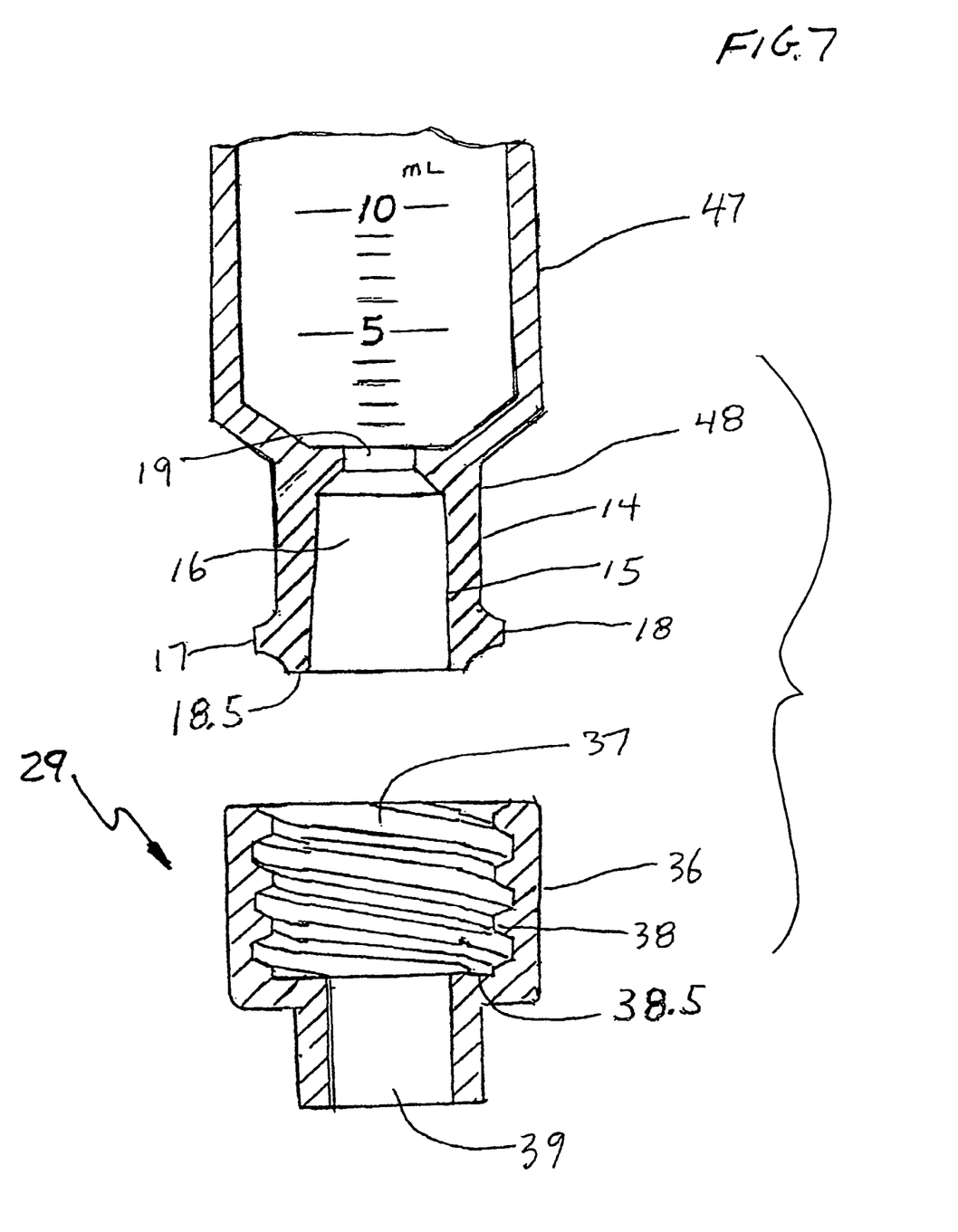
FIG. 7 is a partial cross-sectional view of a standard ISO 80369-3 syringe with tip engageable with the standalone second part of the high flow enteral connector system of the present invention.

FIG. 7 depicts a standard ISO 80369-3 syringe 47 having a standard ISO 80369-3 tip 48 identical in configuration and dimensions to the prior art small bore female connector 11 shown and described in FIG. 1. As such, standalone second part connector 29 of the present invention will readily accept and connect with any existing ISO connector tip. As such, second part connector 29 can receive and accept any ISO 80369-3 syringe having an ISO 80369-3 compatible thread tip 48. Such syringes can be any volume, even the small accurate dose medication syringes of 1, 2, 3, 5 and 10 ml volumes such as ISO 80369-3 compatible accurate dose syringes marketed by NeoMed Inc. as its Low Dose Tip ENFit® Syringe having an internal small tip flow path of only about 1 mm.

Other low dose accurate syringes having an ISO 80369-3 compatible thread tip 48 and having an internal small-bore tip flow path of about 1 to 2 mm could also be designed and produced.

Figure 8:
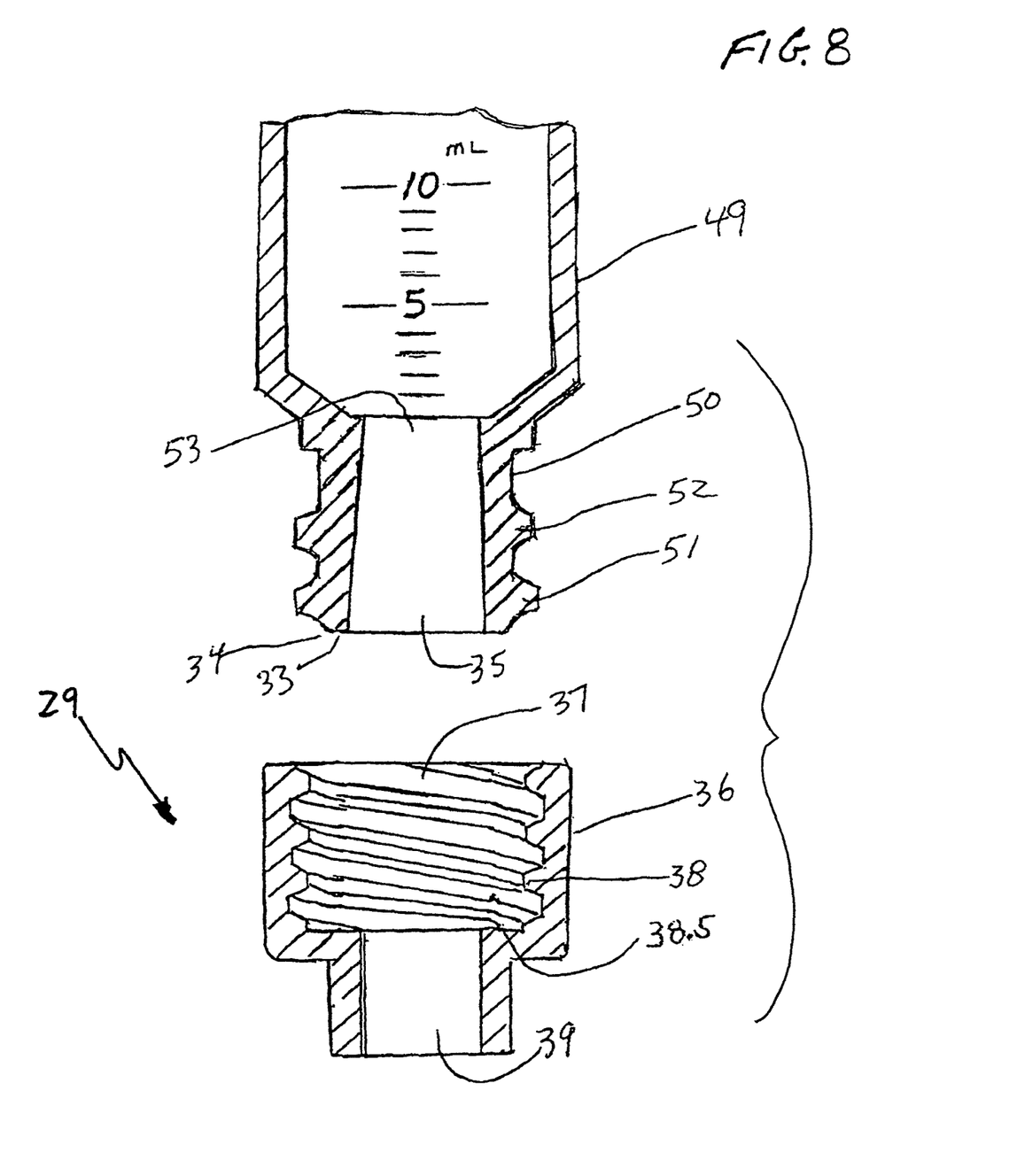
FIG. 8 is a partial cross-sectional view of a high flow enteral syringe having a first part tip engageable with the second part of the high flow enteral connector system of the present invention.

Similarly, FIG. 8 depicts how the standalone second part 29 of the present invention can also readily engage with and accept a high flow enteral syringe 49 having a high flow tip 50. The tip 50 has the same tapered tip projection 33 and high flow inner passageway 35 along with the corner radius 34 along with high flow inlet passageway 53 that is increased to 5.7 mm when the first part tip 50 is threadably engaged with standalone part 29. In addition, the first part tip 50 can have full threads 51 and 52 if desired instead of the partial lug threads 31 and 32 depicted in first part 28 from FIG. 2. Full threads 51 and 52 give added strength to high flow syringe tip 50 to resist breakage during excessive mating thread engagement.

As can be seen from FIGS. 7 and 8, the standalone second part 29 will provide the same fluid tight compressive contact sealing engagement whether a second part 29 is used with an ISO tip 48 from FIG. 7 or a high flow tip 50 depicted in FIG. 8.

Figure 9:
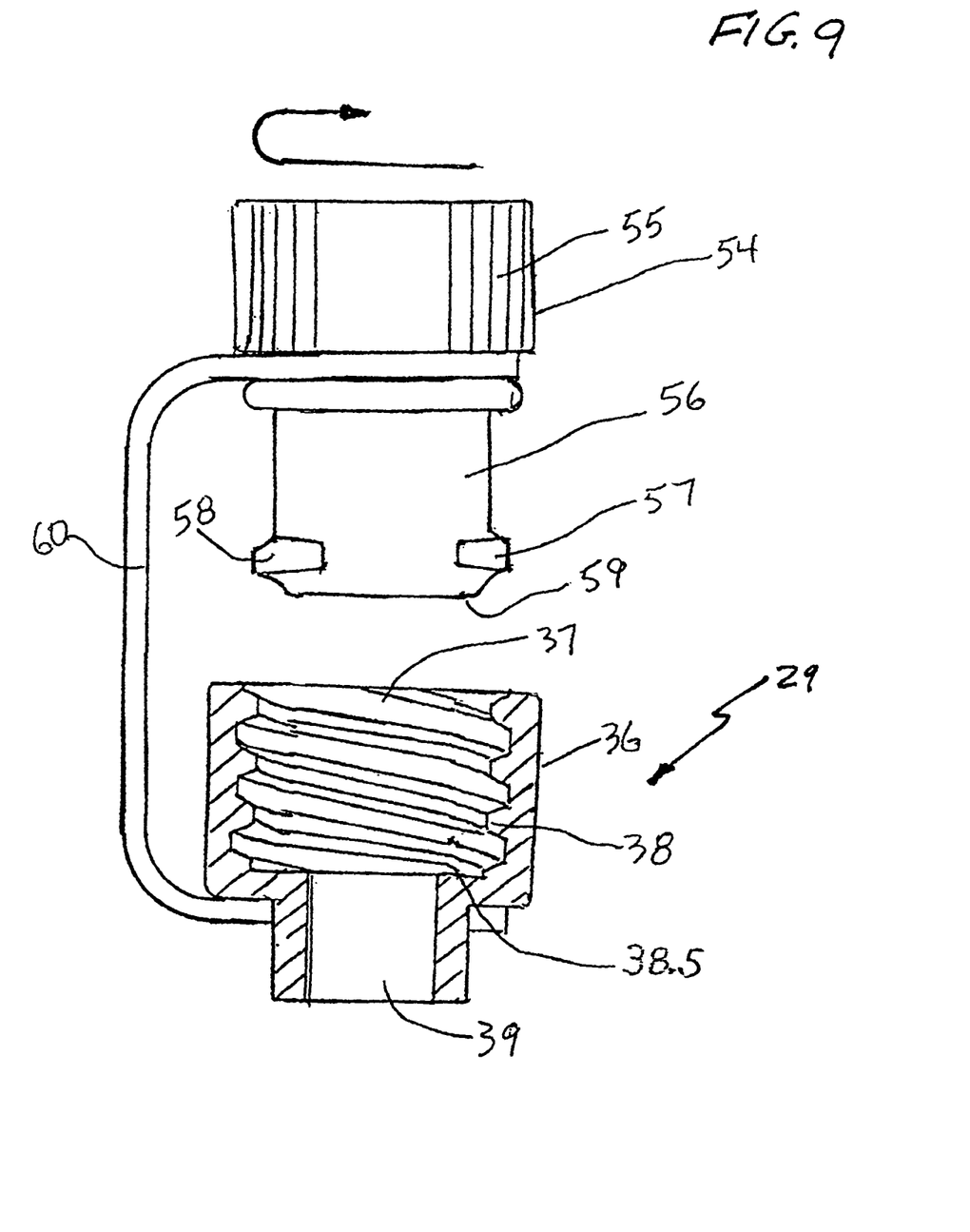
FIG. 9 is a cross-sectional view of the second part of the high flow enteral connector system of the present invention accompanied with a tethered screw cap for closing off the second part when the system is not in use.

FIG. 9 is a cross-sectional view of the standalone second part 29 accompanied with a tethered screw cap closure 54 having a molded in screw cap 55 that turns clockwise along with molded in tip 56. The tip 56 has molded in threads 58 and 57 that form a mating fluid tight seal with second part internal threads 38. The tip 56 has a closed sealed bottom 59 that seals off inner passageway 37 on second part 29 to prevent any back spillage out the second part 29 passageway 37 when the second part 29 is attached to a feeding tube. The tethered strap 60 retains cap 54 on second part 29 to prevent cap 54 from becoming lost during usage of second part 29.

Figure 10:
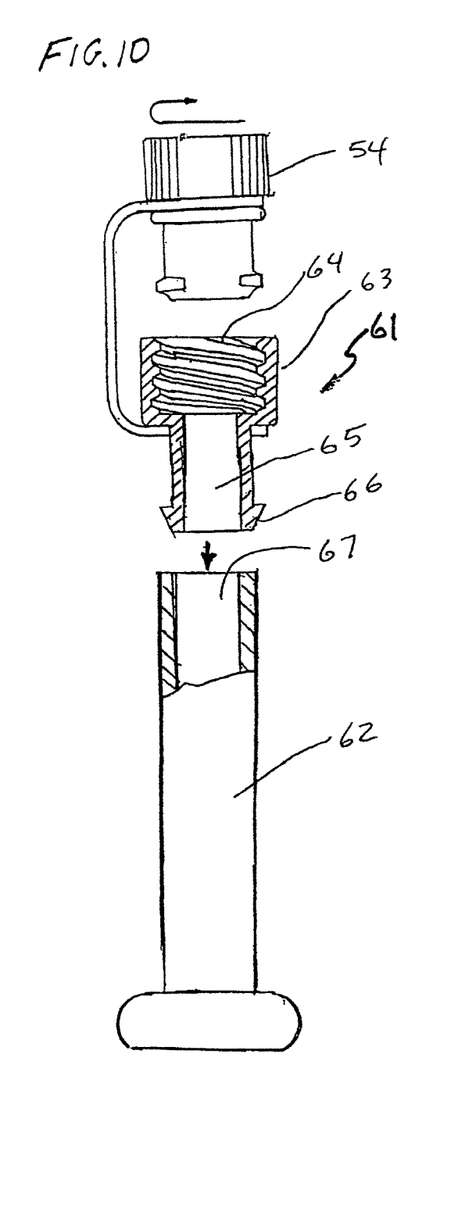
FIG. 10 is a partial cross-sectional view of the standalone second part of the high flow enteral connector of the present invention used as a gastrostomy tube enteral connector adapter.

FIG. 10 is a partial cross-sectional view of the standalone second part connector 61 taking the form of an enteral adapter for use with any type of indwelling gastrostomy tube 62. The connector 61 has an upper portion 63 that is identical in dimensions and performance as all the second parts shown and described as second part 29 from FIGS. 2 and 5. Sealing off the upper portion 63 is cap 54 as shown and described in FIG. 9.

The upper portion 63 has a large opening 64 of up to 8.5 mm and an interior fluid flow path 65 of up to 5.75 mm. The connector 61 terminates in barbed end 66 which can form a press fit with the tubing interior 67 on gastrostomy tube 62. The high flow standalone second part connector 61 is ideal for connection to a wide variety of gastrostomy tubes from 18 fr up to 28 fr that require a large flow path to administer all types of enteral formula especially viscous blenderized food.

Figure 11:
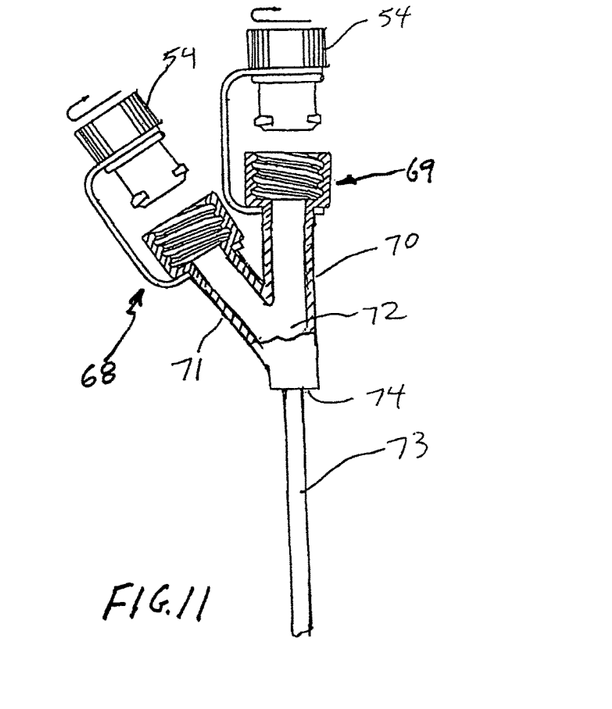
FIG. 11 is a partial cross-sectional view of the standalone second part of the high flow enteral connector of the present invention used as a dual port enteral connector adapter for use in a naso-enteric tube.

Interior opening 64 has no crevice or moat area to trap accumulated formula and is easy to maintain and keep clean due to the interior opening's wide 8.5 mm opening especially when compared to the male small-bore connector 12 depicted in the prior art from FIG. 1. Likewise, FIG. 11 depicts the second part connectors 68 and 69 that may be injection molded from resilient Pellathane® polyurethane of 85 Shore A durometer used as a dual port connector adapter 70. The standalone connectors 68 and 69 are functionally identical to the second part connector 61 depicted in FIG. 10 except that dual port 70 is molded in a Y formation 71 joined in a central fluid flow passageway 72 which can be connected to any naso-enteric feeding tube 73 using a medical grade adhesive joint 74. As such, second part connectors 68 or 69 illustrate how the second part connector of the present invention can be unitized and integrally attached and formed as part of a feeding tube 73. In use, port 69 typically is used as the main connector enteral formula delivery connector port whether administered by pump, gravity or bolus syringe while port 68 is a side port normally used for in-line syringe flushing, medication delivery or tube irrigation.

The connector 61 from FIG. 10 along with connectors 68 and 69 from FIG. 11 show the versatility of the two part high flow enteral system 27 shown and described in FIGS. 2 and 5 wherein the system 27 can be utilized in all types of enteral connections such as percutaneous endoscopic gastrostomy (PEG) tubes, replacement balloon gastrostomy tubes, low profile gastrostomy extension sets, small-bore naso-enteric tubes as well as feeding tube adapters and connectors.

The versatility is achieved because of the fact that the first part can be either the high flow part 28 shown in FIG. 2 or can be the existing ISO first part 11 shown in FIG. 1 while the standalone second part 29 shown and described in FIG. 2 can be used with both of the foregoing parts, that is, high flow part 28 or ISO first part 11, to achieve the desired high flow performance to prevent clogging and flow restriction.

Variations in assembly methods or inlet or outlet attachments can easily take place without departing from the underlying fundamental broad principles of the present invention. For example, the first part 28 can be utilized as an enteral formula administration or delivery set line connector for pump or gravity flow administration wherein the tubing line can be solvent or adhesive joined to the inlet side of the first part 28 and can be single patient use, disposable. Likewise, the second part 29 can have any type of exit configuration or feeding tube connection such as barbs shown in FIG. 10 or gradually increasing dimensioned steps to fit into different sized tubes. In addition, the exit connector port dimension on the second part 29 can also be customized to match the feeding tube internal flow path diameter of choice. Further, the second part 29 can be a replaceable single patient use component for use in any type of feeding tube such as a replacement balloon gastrostomy tube.

Figure 12:
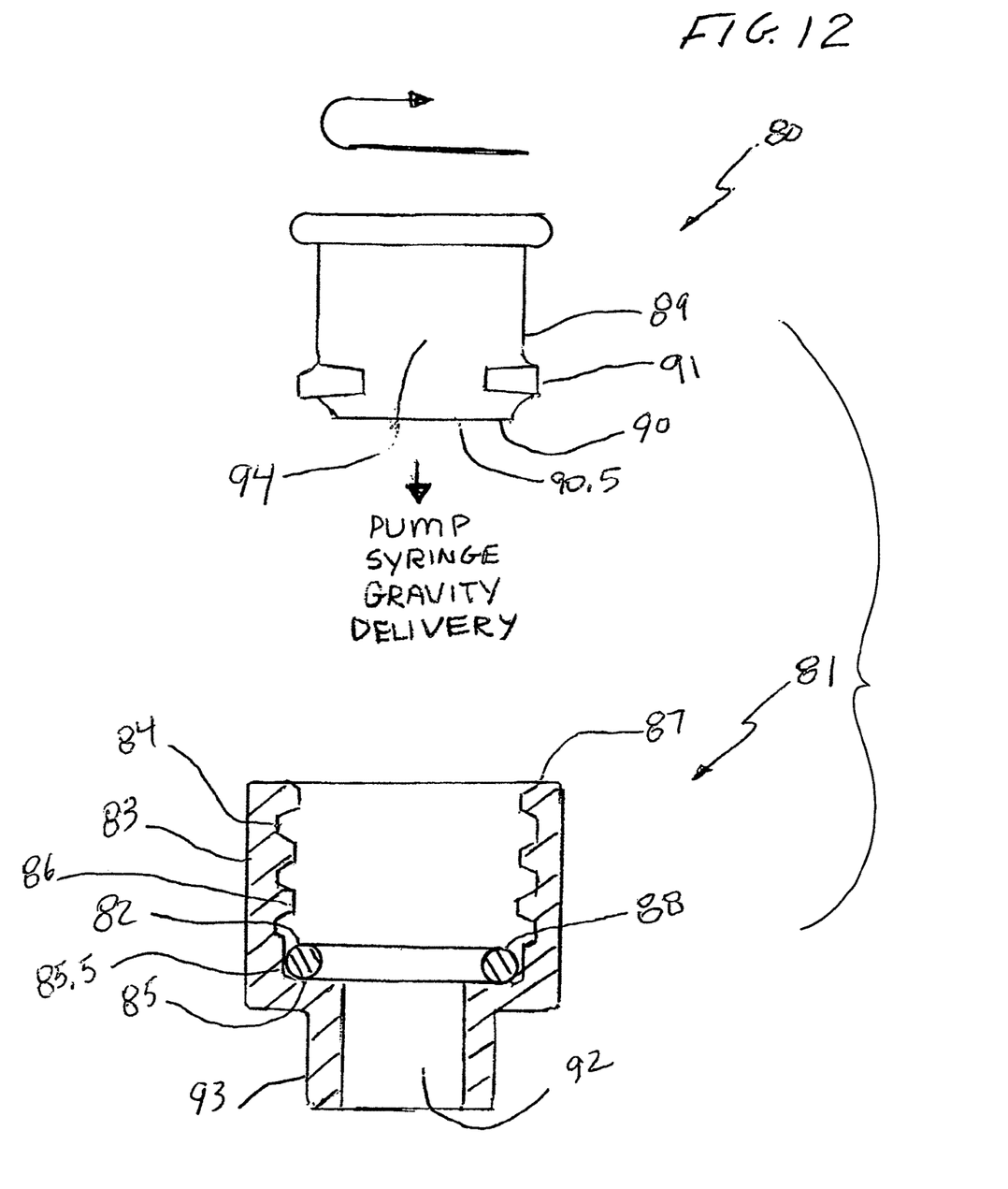
FIG. 12 is cross-sectional view of the second part of the high flow enteral connector system of the present invention having an internal "O" ring forming a compressive leak-proof seal with the first part.

This versatility is also illustrated in FIG. 12 wherein the first part connector 80 is shown capable of being threadably engageable with the second part 81. As can be seen, the first part 80 can take the form of any dimensionally compliant standard ISO connector whether a pump, bolus, syringe or gravity, enteral delivery system as previously shown and described in FIG. 2 and FIG. 7 as well as the high flow bolus syringe shown and described in FIG. 8.

What is different, however, is the modified structure shown as the second part 81 now incorporates resilient "O" ring 82, e.g., Shore 70A silicone, that is press fitted into the injection molded housing 83. The housing 83 has the standard ISO compatible molded in internal threads 84 and "O" ring 82 now rests upon flat internal surface 85. The "O" ring 82 is typically 9.5 mm in outside diameter with a 1.7 mm cross section of the "O" ring portion. The 9.5 mm outside diameter of "O" ring 82 will slightly press fit down over the 8.5 mm maximum internal threads 86 to capture the "O" ring within the housing 83. The insertion depth between the top surface 87 on housing 83 and the top surface 88 on "O" ring 82 is 5.2 mm which is less than the length 89 of 6.82 mm on first part 80. This insures that the circular rigid seal projection 90 on the first part 80 will always provide a resilient compressive sealing engagement with internal sealing surface 85 on the "O" ring 82 positioned below internal thread element 84. The circular sealing surface area "O" ring 82 is positioned at the bottom end 84.5 of the thread depth length 86 within the circular housing 83. The "O" ring 82 may have a round cross-sectional thickness of 1/16", which is 1.7 mm, in cross-section and is commercially available as a standard dash number 010 "O" ring.

Once the external ISO threads 91 on the first part 80 fully manually threadably engage with the internal threads 84 on the second part 81, the circular tip projection portion 90 positioned at the outlet end 90.5 of the internal fluid flow passageway 94 on the first part 80 will form a fluid tight compressive contact sealing engagement with the resilient internal circular sealing surface area 88 on "O" ring 82 within the second part 81. This fluid tight compressive contact sealing engagement withstands a backpressure in excess of 15 psi, which is the maximum back leak pressure provided by an enteral delivery pump or syringe if the enteral feeding tube were to become clogged. As such, liquid enteral nutrition is permitted to flow between fluid flow passageway 94 on the first part connector 80 and the fluid flow passageway 92 on the second part connector 81 without leakage when first part connector 80 is fully threadably engaged with the internal mating thread engagement element 84 on the second part 81.

The second part 81 internal fluid flow passageway 92 is still maintained to provide a maximum internal flow path up to 5.3 mm although the typical passageway would be about 4 mm in diameter which matches the internal fluid flow passageway of traditional 60 cc catheter tip enteral syringes which is in excess of the limiting 2.95 mm internal fluid flow passageway of the ISO 80369-3 Standard second part connector 12 shown and described in prior art FIG. 1. This increased high flow passageway can now permit even viscous blenderized food to pass successfully through the connector system of the present invention. While an "O" ring design is shown and described in FIG. 12, it is also contemplated that a flat resilient washer, gasket or even an insert molded resilient gasket made from resilient synthetic rubber such as Dynaflex® can also provide a similar internal circular sealing surface area as the "O" ring 82 design.

Similarly, the distal end 93 on second part connector 82 can take any form of feeding tube engagement as previously shown and described in FIGS. 10 and 11 and the second part 81 can receive enteral formula delivered by pump, bolus, syringe or gravity delivery as well as crushed and dissolved medications from the first part 80. As such, the first part connector 80 is fully dimensionally compliant with the ISO 80369-3 Standard while the second part 81 has been modified to be threadably compatible with the ISO 80369-3 Standard to provide an internal high flow fluid flow passageway in excess of the limiting 2.95 mm internal fluid flow passageway of the ISO 80369-3 Standard.

Figure 13:
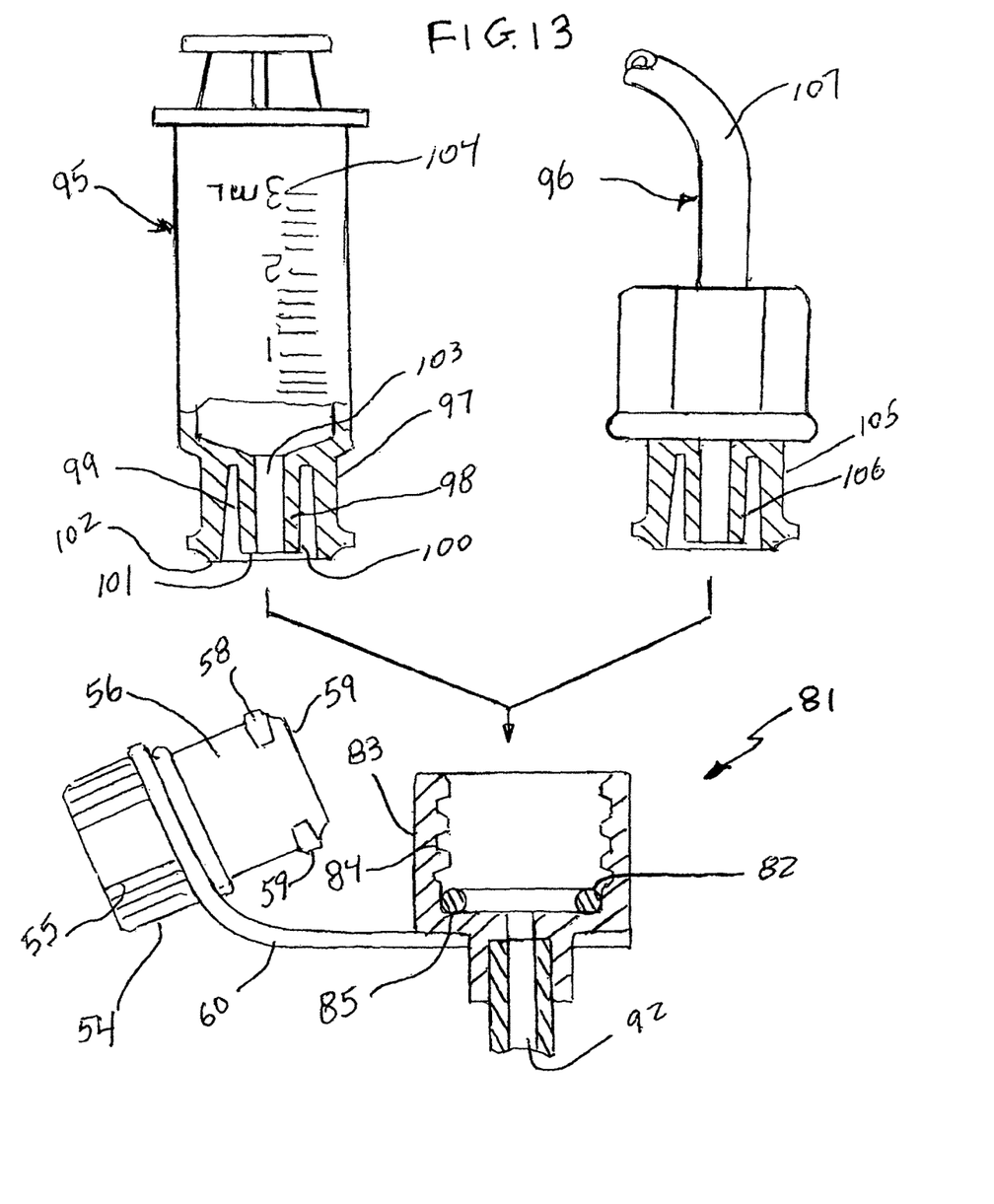
FIG. 13 is a cross-sectional view of the second part connector having an internal "O" ring from FIG. 12 depicting the second part connector engageable with an accurate dosage syringe or an accurate dosage enteral delivery extension set.

FIG. 13 further illustrates the versatility of second part connector 81 illustrated and described from FIG. 12 having screw cap closure 54 with screw cap 55 along with tethered strap 60 identical to the screw cap 55 and tethered strap 60 shown and described from FIG. 9. The second part 81 includes a housing 83 having ISO 80369-3 compatible molded-in internal threads 84 along with the "O" ring 82. ISO 80369-3 internal threads 84 permit a leakproof connection and threaded engagement with all first part connectors previously shown and described as first part connector 11 from FIG. 1 as well as any ISO 80369-3 syringe 47 shown and described in FIG. 6. In addition, second part connector 81 from FIG. 13 will also form a positive leakproof screw thread sealing engagement with an accurate dose syringe 95 as well as an accurate dose extension set 96 also depicted in FIG. 13.

An accurate dose syringe 95 is shown in FIG. 13 and has an ISO 80369-3 threadably compatible distal end 97 incorporating a unique internal tip 98 having an outside diameter 99 of 3.5 mm and an external length 100 of about 4 mm. The tip 98 is also slightly recessed 101 about 1 mm from circular distal end tip projection 102. Most importantly, tip 98 has a small volume flow path internal diameter 103 between 1 mm up to 2.95 mm and a length of 5 mm whose volume does not exceed 0.07 ml that does not exceed the maximum allowable residual tip volume of 0.07 ml as defined in ISO 7886-1 syringe accuracy standard.

Other commercial manufacturers' attempts at an accurate dose ISO 80369-3 compatible syringe tip limits the outside diameter to a maximum of 2.85 mm and therefore limits the inside diameter to a maximum of only 1.45 mm. This limitation is because the 2.85 mm outside diameter must fit inside the second part ISO 80369-3 connector's male connector 2.95 mm I.D. passageway 22 part of prior art male connector 12 as shown in prior art FIG. 1. This inside diameter limitation severely limits the internal flow path of the second part syringe tip to a maximum of only 1.45 mm, whereas the current invention of an accurate dose syringe 95 has an internal flow path of up to 2.95 mm.

The present invention internal tip 98 having a 1 mm up to 2.95 mm internal diameter 103 provides an accurate dosage of medication delivery in syringes having a volume 104 of less than 30 ml as shown in FIG. 13. As such, accurate dose syringe 95 is especially useful in administration of accurate dose medication in critically ill adults, adolescents, neonates and children. Since the accurate dose syringe 95 is precise in delivering accurate administration of medication, the syringe 95 can also be utilized as a standalone syringe for aspiring liquid or dissolved crushed medication and can be used as a standalone oral medication-administering syringe. This dosage accuracy is very important in low dose liquid syringes having low small volumes of 1 ml, 2 ml, 3 ml, 5 ml and 10 ml used with infants, children and adults. Dosage accuracy is also true in the first part accurate dose extension set 96 also shown in FIG. 13 and also having an ISO 80369-3 threadable compatible distal end 105 incorporating the same unique internal tip 106 identical in structure and performance as distal end 97 and tip 98 shown and described as part of the accurate dose syringe 95 also from FIG. 13.

An accurate dose extension set 96 also forms a threadable leakproof engagement with the second part connector 81 having a built-in "O" ring 82 and can deliver accurate dose enteral formula from a pump or gravity administration line 107 or even from a special enteral formula gravity squeezable delivery pouch or bag. As such, the first part of the system can be an accurate dose syringe 95 or an accurate dose enteral delivery set 96 as shown and described in FIG. 13.

Figure 14:
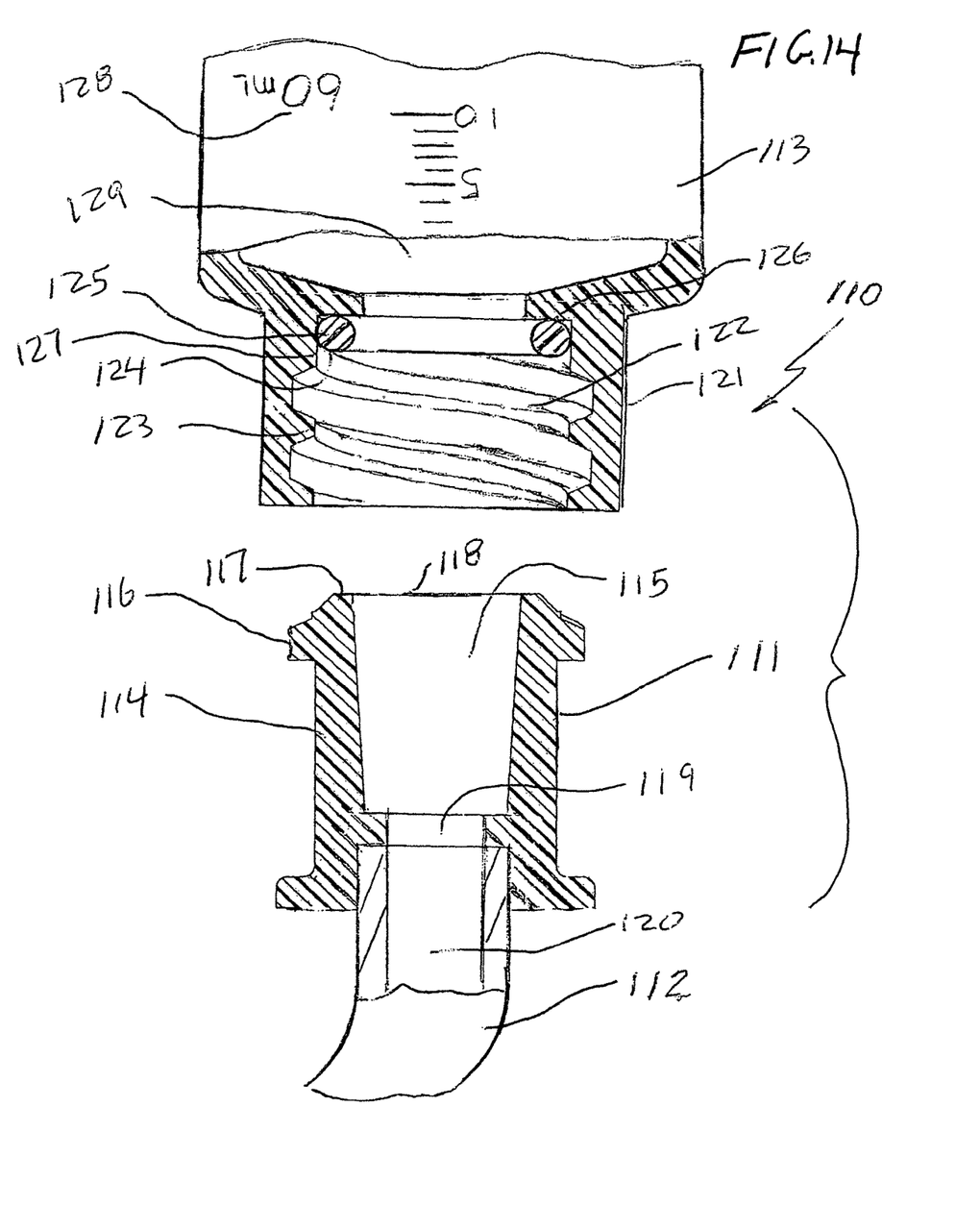
FIG. 14 is a cross-sectional view of the high flow enteral connector system of the present invention wherein the orientation of the system is reversed such that the first part is the feeding tube receiving part and the second part is the syringe or delivery set side.

The versatility of the high flow characteristics of the present two-part enteral connector system is further illustrated in FIG. 14 wherein the two-part system 110 is reversed. The first part connector 111 is the receiving feeding tube 112 on the patient's side and the second part 113 is positioned on the second part connector syringe or delivery set side.

The first part connector 111 is injection molded from rigid plastic such as ABS and comprises outer housing 114 with a socket configured internal fluid flow passageway 115 with external thread element 116 and a circular tip projection portion 117 positioned at the outlet end 118 of the internal fluid flow passageway 115. Dimensionally, the first part connector is fully compliant with the female E1 Small-Bore Connector part from the ISO ANSI 80369-3 standard with the added advantage that feeding tube inlet passageway 119 can now be a high flow passageway of up to 5.5 mm in internal diameter instead of the standard restricted 2.95 mm internal diameter of the ISO ANSI 80369-3 standard. This significant increase in flow diameter of up to 5.5 mm can now provide an unrestricted fluid flow passageway 120 for tubes up to 24 FR.

This increase in flow diameter is especially advantageous for the tube fed patient who requires large French size tubes up to 24 FR to administer non-clogging administration of commercial enteral formula as well as viscous home-blenderized food which the ISO 80369-3 Standard 2.95 mm internal diameter simply cannot accommodate as previously explained. The ISO 80369-3 Standard restrictive flow path of 2.95 mm from the existing commercially available ISO connectors requires either excessive pump pressure or excessive manual syringe force well above 10 pounds of force when administering viscous formula or blenderized food. Most at-home feeders simply cannot apply that amount of syringe force.

To further enhance the high flow characteristics of the two-part system 110, the second part connector syringe or delivery set side 113 has a circular housing 121 with an internal fluid flow passageway 122 wherein the housing 121 has a mating internal thread engagement element 123 that threadably mates with external thread engagement element 116 on the housing 114 on the first part connector 111. The injection molded circular housing 121 on the second part connector 113 includes a resilient internal circular sealing surface area 124 which may take the form of a 70 Shore A silicone molded resilient "O" ring 125 positioned at the bottom end 126 of the internal thread element 123 depth length 127 within housing 121.

The internal thread element 123 is fully dimensionally compliant with the male small-bore connector portion of ISO 80369-3 Standard such that the external thread element 116 on the first part 111 will threadably mate with the internal thread engagement element 123 on the second part connector 113. Once threadably engaged, the circular tip projection portion 117 on the first part connector 111 forms a fluid tight compressive contact sealing engagement with the resilient internal circular sealing surface area 124 within second part connector 113 when the first part external thread element 116 is fully threadably engaged with the mating internal thread engagement element 123 on the second part connector 113.

The second part connector 113 can therefore take the form of any syringe or enteral formula pump or gravity delivery set, but can be especially useful when configured as a large volume 60 ml enteral syringe 128 with a high flow inlet 129 of up to 5.5 mm in internal diameter which matches the 5.5 mm high flow feeding tube inlet passageway 119 on the patient side feeding tube on the first part connector 111 to provide low pressure syringe pressure of less than 2 pounds of force. As such, the versatility of the high flow enteral connector system of the present invention can be oriented as shown and described in FIG. 8 through 13 or can be reversed as shown and described in FIG. 14.

Regardless of the orientation, the two-part connector system provides far superior high flow performance while remaining threadably compliant with the existing ISO/ANSI 80369-3 Small-Bore Enteral Connector Standard. All these variations can be accomplished by those skilled in the medical field engineering art while still utilizing and maintaining the unique features of the basic underlying structure and characteristics of the high flow enteral connector system of the present invention.

While there is shown and described herein certain specific structure embodying this invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A two part threadably engageable and disengageable ISO 80369-3 medical connector system not mating with I.V. luers for preventing any interlocking or threadable fit with an ISO ANSI 1986 Standard luer dimensioned syringe tip or connector comprising:

a first part ISO 80369-3 dimensionally compliant enteral fluid delivery side connector capable of delivering pressurized enteral fluid by enteral pump or syringe and a mating second part structurally modified ISO 80369-3 compatible enteral fluid receiving side connector;

said second part fluid receiving side connector structurally modified to include an outer housing having an internal thread engagement and disengagement element with a thread depth length and a bottom end where an internal fluid passageway is located, and a resilient internal circular sealing surface area "O" ring insertably pressed fit into the bottom end of the thread depth length to capture and retain said "O" ring within said outer housing below the internal thread engagement and disengagement element;

wherein said internal thread engagement and disengagement element has an internal diameter that is less than the diameter of said "O" ring, thereby preventing the "O" ring from falling out of the bottom end of the housing when disengaged from a syringe tie;

said resilient internal circular sealing surface area "O" ring forming and maintaining a fluid tight compressive contact sealing engagement with the first part fluid delivery side connector when said first part fluid delivery side connector is fully threadably engaged with the second part fluid receiving side connector, and the resilient internal circular sealing surface area "O" ring maintaining the fluid tight compressive contact sealing engagement when the first part fluid delivery side connector delivers pressurized enteral fluid by enteral pump or syringe.

2. The connector system of claim 1 wherein the first part enteral fluid delivery side connector is also capable of delivering enteral fluid by a bolus syringe or gravity delivery device.

3. The connector system of claim 1 wherein said resilient internal circular sealing surface area "O" ring has a round cross-section.

4. The connector system of claim 1 wherein said resilient internal circular sealing surface area "O" ring has a flat cross-section.

5. The connector system of claim 1 wherein the resilient internal circular sealing surface area "O" ring is a synthetic rubber.

6. The connector system of claim 1 wherein said resilient internal circular sealing surface area "O" ring is molded into the bottom end of the housing.

7. The connector system of claim 1 wherein the second part structurally modified ISO 80369-3 compatible enteral fluid receiving side connector is utilized as a standalone enteral feeding tube adapter or joined as part of a feeding tube assembly.

8. The connector system of claim 1 wherein the second part bottom end internal fluid passageway has a flow path up to 5.3 mm diameter.

9. The connector system of claim 1 wherein the second part structurally modified ISO 80369-3 compatible enteral fluid receiving side connector can threadably engage with existing ISO 80369-3 first part enteral fluid delivery side connectors.

10. A two part threadably engageable and disengageable ISO 80369-3 medical connector system not mating with I.V. luers for preventing any interlocking or threadable fit with an ISO ANSI 1986 Standard luer dimensioned syringe tip or connector comprising:
a first part ISO 80369-3 dimensionally compliant enteral fluid delivery side connector capable of delivering pressurized enteral fluid by enteral pump or syringe and a mating second part structurally modified ISO 80369-3 compatible enteral fluid receiving side connector utilized as part of an enteral feeding tube;
said second part fluid receiving side connector structurally modified to include an outer housing having an internal thread engagement and disengagement element with a thread depth length and a bottom end where an internal fluid passageway is located, and a resilient internal circular sealing surface area "O" ring insertably positioned into the bottom end of the thread depth length to capture and retain said "O" ring within said outer housing;
wherein said internal thread engagement and disengagement element has an internal diameter that is less than the diameter of said "O" ring, thereby preventing the "O" ring from falling out of the bottom end of the housing when disengaged from a syringe tip;
said resilient internal circular sealing surface area forming and maintaining a fluid tight compressive contact sealing engagement with the first part fluid delivery side connector when said first part fluid delivery side connector is fully threadably engaged with the second part fluid receiving side connector.

11. The connector system of claim 10 wherein said resilient internal circular sealing surface area is molded from a synthetic rubber.

12. The connector system of claim 10 wherein said resilient internal circular sealing surface area "O" ring has a round cross-section.

13. The connector system of claim 10 wherein said resilient internal circular sealing surface area "O" ring has a flat cross-section.

14. The connector system of claim 10 wherein the second part structurally modified ISO 80369-3 compatible enteral fluid receiving side connector can threadably engage with existing ISO 80369-3 first part enteral fluid delivery side connectors.

15. The connector system of claim 10 wherein the second part bottom end internal fluid passageway has a flow path up to 5.3 mm in diameter.

16. A two part threadably engageable and disengageable ISO 80369-3 medical connector system not mating with I.V. luers for preventing any interlocking or threadable fit with an ISO ANSI 1986 Standard luer dimensioned syringe tip or connector comprising:
a first part existing ISO 80369-3 dimensionally compliant enteral fluid delivery side connector and a mating second part structurally modified ISO 80369-3 threadably compatible enteral fluid receiving side connector;
said second part structurally modified ISO 80369-3 threadably compatible enteral fluid receiving side connector including an outer housing having an internal thread engagement and disengagement element with a thread depth length and a bottom end where an internal fluid passageway is located, and a resilient internal circular sealing surface area "O" ring insertably press fit into the bottom end of the thread depth length is to capture and retain said "O" ring within said outer housing;
wherein said internal thread engagement and disengagement element has an internal diameter that is less than the diameter of said "O" ring, thereby preventing the "O" ring from falling out of the bottom end of the housing when disengaged from a syringe tip; and
said resilient internal circular sealing surface area forming and maintaining a fluid tight compressive contact sealing engagement with the first part existing ISO 80369-3 dimensionally compliant enteral fluid delivery side connector when said first part existing ISO 80369-3 dimensionally compliant enteral fluid delivery side connector is fully threadably engaged with the second part structurally modified ISO 80369-3 compatible enteral fluid receiving side connector.

17. The connector system of claim 16 wherein the second part structurally modified ISO 80369-3 compatible enteral fluid receiving side connector can receive fluid delivered by pump, bolus, syringe or gravity.

18. The connector system of claim 16 wherein the bottom end internal fluid passageway of the second part structurally modified ISO 80369-3 threadably compatible enteral fluid receiving side connector has a flow path up to 5.3 mm in diameter.

19. The connector system of claim 16 wherein the resilient internal circular sealing surface area "O" ring is a synthetic rubber.

20. The connector system of claim 16 wherein said resilient internal circular sealing surface area "O" ring has a round cross-section.

21. The connector system of claim 16 wherein said resilient internal circular sealing surface area "O" ring has a flat cross-section.

22. The connector system of claim 16 wherein said resilient internal circular sealing surface area "O" ring is molded into the bottom end of the housing.

23. The connector system of claim 16 wherein the second part structurally modified ISO 80369-3 compatible enteral fluid receiving side connector can threadably engage with existing ISO 80369-3 first part enteral fluid delivery side connectors.

* * * * *

UNITED STATES PATENT AND TRADEMARK OFFICE
CERTIFICATE OF CORRECTION

PATENT NO. : 10,918,848 B1  
APPLICATION NO. : 15/731481  
DATED : February 16, 2021  
INVENTOR(S) : Russo et al.

Page 1 of 1

It is certified that error appears in the above-identified patent and that said Letters Patent is hereby corrected as shown below:

On the Title Page

Item (54) and in the Specification, Column 1, Lines 1-2, should read High Flow Enteral Connector System Replace Drawing with Figure 12 Drawing Signed and Sealed this  
Thirtieth Day of November, 2021

Drew Hirshfeld  
*Performing the Functions and Duties of the*  
*Under Secretary of Commerce for Intellectual Property and*  
*Director of the United States Patent and Trademark Office*